United States Patent [19]

Kokusho et al.

[11] 3,950,221
[45] Apr. 13, 1976

[54] PROCESS FOR IMPROVING THE QUALITY OF MICROBIAL RENNET

[75] Inventors: Yoshitaka Kokusho, Kunitachi; Susumu Higashi, Fuchu; Haruo Machida; Shinjiro Iwasaki, both of Hino, all of Japan

[73] Assignee: Meito Sangyo Kabushiki Kaisha, Nagoya, Japan

[22] Filed: July 22, 1974

[21] Appl. No.: 490,278

[30] Foreign Application Priority Data
Aug. 2, 1973  Japan.................. 48-86396

[52] U.S. Cl.................. 195/65; 195/66 R; 426/36
[51] Int. Cl.$^2$.................. C07G 7/02; A23C 19/00
[58] Field of Search.................. 195/66 R, 65

[56] References Cited
UNITED STATES PATENTS

| | | | |
|---|---|---|---|
| 2,683,682 | 7/1954 | Miller et al. | 195/66 R |
| 3,549,390 | 12/1970 | Charles et al. | 195/66 R X |
| 3,591,388 | 7/1971 | Moelker et al. | 195/66 R X |
| 3,616,233 | 10/1971 | Schleich | 195/66 R |

OTHER PUBLICATIONS

Chemical Abstracts, Vol. 73, 108414j (1970).

Chemical Abstracts, Vol. 76, 111775v (1972).

*Primary Examiner*—Lionel M. Shapiro
*Attorney, Agent, or Firm*—Sherman & Shalloway

[57] ABSTRACT

A process for improving the quality of microbial rennet by inactivating cellulase impurities in microbial rennet which comprises heat-treating microbial rennet in an aqueous medium in the presence of sodium chloride.

4 Claims, No Drawings

PROCESS FOR IMPROVING THE QUALITY OF MICROBIAL RENNET

This invention relates to a process for improving the quality of microbial rennet, and more specifically, to a process for improving the quality of microbial rennet by inactivating cellulase impurities in microbial rennet which comprises heat-treating microbial rennet in an aqueous medium in the presence of sodium chloride.

In the generally practiced art of cheesemaking, milk is clotted or coagulated by the enzymatic action of milk-clotting enzyme, to form a curd, the curd is cut into multiple pieces, and the pieces of curd are cooked to separate the liquid whey. The collected curd is then enveloped in a cheese cloth or a cheese bandage and pressed for several days. The green cheese so obtained is cured in a fermentation chamber for several months to form the desired cheese product.

The enzyme usually employed in the art to produce the curd by clotting or coagulation of milk is the enzyme rennin found in calf rennet which is obtained by the extraction of the mucosa of the fourth stomach of unweaned calves.

With an increased output of cheese production in recent years, the relative shortage of calf rennet supply has prompted many attempts to develop a suitable substitute for calf rennet. A variety of microbial enzymes have emerged from these studies, and some of them are commercially utilized in the production of cheese. These are prepared, for example, from *Mucor pusillus* and *Mucor miehei*.

The cloth, commonly used as a cheese bandage in the practiced art of cheesemaking, is made of cellulose fibers such as cotton.

Microbial rennet preparations frequently contain cellulase impurities which sometimes cause the disadvantage of disintegration and/or reducing the durability of the cloth.

We have made investigations with a view to overcoming the above disadvantage and found that by a simple means of heat-treating microbial rennet in an aqueous medium in the presence of sodium chloride, the cellulase impurities can be conveniently inactivated without substantial loss of milk-clotting activity in the microbial rennet.

Thus, it has been found that the above described simple means can provide microbial rennet of improved quality which does not exert adverse effects on the cheese cloth.

Accordingly, the primary object of this invention is to provide a process for preparing microbial rennet of improved quality, and other objects and advantages of this invention will become clear in the following description.

Microbial rennets useful as raw materials for the process of the present invention can be obtained by methods known in the prior art. They can be prepared by growing under aerobic conditions a culture of such known microorganisms as *Mucor pusillus*, *Mucor miehei*, *Endothia parasitica*, *Bacillus polymyxa*, *Bacillus subtilis* and *Rhizopus oligosporus*, in a medium containing appropriate nutrients and then recovering the enzyme therefrom.

The process of the present invention is comprised of heat-treatment of microbial rennet in various forms. It can be in the form of aqueous whole cultures or fermentation beers, or filtrate thereof, or extract of fermented koji or concentrate thereof, or in the form of a microbial rennet containing solution of each step in recovering and purifying therefrom. It can also be in the form of dried material or precipitated material with organic solvents or with salts as is known in the art, which are then dissolved in water or appropriate aqueous media for use in the present process.

The concentration of the microbial rennet in the aqueous medium is not critical, unless the volume of the aqueous medium is so small as to prevent the dissolution of sodium chloride. It is generally preferable to use microbial rennet of higher concentration in the process of the present invention and this gives better operating efficiency. The process of the present invention is carried out by heat-treatment of microbial rennet in aqueous medium in the presence of sodium chloride. The time of the addition of sodium chloride is not critical, so far as sodium chloride is present at the time of heat-treatment. The presence of sodium chloride will enhance the thermostability of microbial rennet and will promote the inactivation of cellulase impurities at the same time.

The amount of sodium chloride to be present at the time of heat-treatment can be selected from any desired amounts up to saturation according to the concentration of the microbial rennet-containing liquid.

Generally, a higher concentration of sodium chloride is desirable in order to minimize the inactivation of the milk-clotting activity of microbial rennet and to maximize the inactivation of cellulase activity. Preferably, the amount of sodium chloride is at least about 5% by weight, especially about 15 to 30% by weight. Where the concentration of the microbial rennet is higher, the same effect can be obtained with lower concentration of sodium chloride.

The process of the present invention is carried out under thermostable pH conditions for the microbial rennet.

Orginally, the thermostable pH range is inherent to each enzyme and is variable according to the properties of the microbial rennet. For example, microbial rennet produced by *Mucor pusillus* is most thermostable at a pH of about 4.0 to 6.0, preferably about 5.0, and microbial rennet produced by *Endothia parasitica*, at a pH of about 4.0 to 5.5 and most preferably about 4.5.

In present application, the term "thermostable pH conditions for the microbial rennet" denote conditions under which the microbial rennet after heat-treatment can retain at least 70% of the original milk-clotting activity.

These conditions are dependent upon such factors as the amount of sodium chloride, the type and concentration of the microbial rennet, or the temperature and period of time of heat-treatment.

Therefore, these conditions can be experimentally determined according to the heating conditions, the amount of sodium chloride, and the type and concentration of the microbial rennet.

In the process of this invention, microbial rennet is heat-treated in an aqueous medium in the presence of sodium chloride in an amount of preferably at least about 5% by weight, more preferably at least about 7% by weight under thermostable pH conditions for the microbial rennet. In order to achieve the maximum removal of cellulase activity, it is desirable to perform the heat-treatment at the highest possible temperatures for the longest possible period of time, unless the milk-clotting activity of the microbial rennet is disadvantageously reduced.

However, the milk-clotting activity will disadvantageously be reduced at unreasonably high temperatures, and excessively low temperatures will require too long periods of treating time, resulting in a reduction of the efficiency of operation.

Accordingly, it is usually recommended to perform the heat-treatment at a temperature of about 45° to 90°C., preferably about 50° to 80°C. for about 5 seconds to about 10 minutes.

It should be understood that much higher temperatures and/or much shorter periods of time can also be employed when the heat-treatment is effected by instantaneous heating means, for example using a plate heat exchanger or spray dryer.

It is desirable that after the heat-treatment, the liquid containing the microbial rennet is rapidly cooled to about 30°C. or less. The microbial rennet-containing liquid so obtained can be directly used for coagulating milk, but it is also possible to recover the microbial rennet as a dry powder by well known techniques.

In the microbial rennet of improved quality obtained by the process of this invention, the cellulase will never be reactivated during storage and the microbial rennet maintains its improved quality.

The process of the present invention is very useful since it can inactivate the cellulase in the microbial rennet easily with good efficiency and without inactivating the milk-clotting activity.

The present invention will be described in more detail in the following examples. It should be understood, however, that they are intended only in an illustrative sense and the scope of the invention should not be limited thereby.

The milk-clotting activity and the cellulase activity of the microbial rennet were measured according to the following methods.

Milk-clotting activity

A 10% (weight/volume basis) solution is prepared by dissolving an appropriate amount of non-fat dry milk solids in 0.01 M calcium chloride solution. A 5 ml aliquot of the above milk solution is placed in a test tube and heated to 35°C. Then, a 0.5 ml portion of enzyme liquid at 35°C is added to the milk solution in the test tube. The enzyme-milk solution mixture is immediately mixed with stirring, and the time to form the first visible flecks of curd is measured. The enzyme concentration is selected so that the clotting time will be about four minutes.

The milk-clotting activity of the microbial rennet is calculated as follows:

$$\text{Soxhlet unit (SU)} = \frac{M}{E} \times \frac{2400}{T}$$

wherein:
 $M$ is the volume of milk solution (ml)
 $E$ is the enzyme weight (g)
 $T$ is the time until the first flecks form (sec.).

The enzyme activity is then expressed in Soxhlet units (SU) per gram. When the enzyme is originally employed in a liquid form, the appropriate volume in milliliters E is used in the above formula, and the enzyme activity is expressed as Soxhlet units per milliliter.

One Soxhlet unit is the amount of enzyme activity which can coagulate 1 ml of the above milk solution in 40 minutes.

Cellulase activity

A 1% (weight/volume basis) solution is prepared by dissolving carboxymethyl cellulose powder in a 0.1 M acetate buffer of pH 5.0. A 3 ml aliquot of this solution is placed in a 25 ml glass-stoppered test tube and tempered to 35°C. A 1 ml portion of enzyme liquid is added to the above carboxymethyl cellulose solution and this mixture is incubated at 35°C for a given period of time. Immediately after the addition of a 3 ml portion of reagent solution (A) to this mixture, the test tube is immersed in a boiling water bath and kept exactly for 10 minutes. After being cooled in tap water, 3 ml aliquot of reagent solution (B) is added and carbon dioxide generated is expelled. A 10 ml portion of 0.3 N sodium hydrooxide solution is added and the mixture is thoroughly blended by vigorous shaking and then the absorbancy at 500 nm is read in the spectrophotometer. The color developed is stable for 3 hours.

As a blank, a 3 ml portion of reagent solution (A) is added to 3 ml of carboxymethyl cellulose solution before the addition of the enzyme liquid, and the absorbance value is obtained according to the same procedure for the test sample.

The absorbancy of the blank is subtracted from that of the sample, then the glucose content is computed from a curve previously established with standard glucose solution.

The cellulose activity is then calculated from the following formula.

$$\text{Cellulose unit (CU)} = \frac{G}{180 \times T \times E}$$

wherein:
 $G$ is the amount (Mg) of glucose
 $T$ is the reaction time (minute)
 $E$ is the amount (g or ml) of microbial rennet.

One cellulase unit is defined as the amount of enzyme which can liberate from carboxymethyl cellulose, reducing material equivalent to 1 $\mu$mol of glucose in a minute under the conditions of the above determination.

Reagent solution (A)

Rochelle salt (12 g) and anhydrous sodium carbonate (24 g) are dissolved in about 250 ml of water and 40 ml of a 10% (weight/volume basis) aqueous solution of cupric sulfate pentahydrate is stirred in, followed by 16 g of sodium bicarbonate. 180 g of anhydrous sodium sulfate is dissolved in 500 ml of hot water and is boiled to expel air and cooled. This solution is combined with the copper solution and diluted to 1 L with water. After incubating for 3 days at 37°C, the filtrate is used as reagent solution (A).

Reagent solution (B)

T0 25 g of ammonium molybdate in 450 ml of water is added 21 ml of concentrated sulfuric acid, followed by 3.0 g of disodium hydrogen arsenate heptahydrate dissolved in 25 ml of water. The mixed solution is stored in a glass-stoppered brown bottle and used as reagent solution (B).

When the cellulase activity is measured by a method using a microcrystalline cellulose powder as a substrate or according to a method to determine the reduction in the viscosity of carboxymethyl cellulose, almost the same results as in the above assay method are obtained.

Example 1 and Comparative Example 1

A culture medium consisting of 10 parts of wheat bran, 0.1 part of ammonium sulfate and 7 parts of water was sterilized and was inoculated with a culture of Mucor pusillus IAM F-27 (IAM : Institute of Applied Microbiology, University of Tokyo), an cultivated for 72 hours at 35°C. A solution of microbial rennet was prepared by extracting the fermented wheat bran koji with water. One ml portion of this solution contained 1.4 CU cellulase and 25,800 SU milk clotting enzyme.

Sodium chloride was added to aliquot portions of this solution to achieve 5%, 10%, 15% and 20% (weight-/volume basis) concentrations respectively and the pH of the solution was adjusted to 5.0. Milk-clotting activities and cellulase acitivities which remained in the resulting solution after the heat treatment at 60°C. for 5 minutes are shown in Table 1.

The values in the table are expressed as percentage to each enzyme activity in the original solution. A blank test without the addition of sodium chloride was carried out for comparison.

TABLE 1

| Run No. | Comparative Example 1 | Example 1 Run 1 | Run 2 | Run 3 | Run 4 |
|---|---|---|---|---|---|
| Concentration of NaCl (%) | 0 | 5 | 10 | 15 | 20 |
| Remaining cellulase activity | 85 | 40 | 30 | 20 | 10 |
| Remaining milk-clotting activity | 91 | 100 | 100 | 100 | 100 |

Example 2 and Comparative Example 2

A microbial rennet-containing extract was prepared as described in Example 1 from Mucor miehei CBS 182.67 (CBS: Centraalbureau voor Schimmelcultures, Baarn, Holland), after cultivation for 96 hours at 35+C and extraction with water. This aqueous solution contained 1.0 CU cellulase and 3,500 SU milk-clotting enzyme in 1 ml. Sodium chloride was added to make a 20% (weight/volume basis) solution and the pH of this solution was adjusted to 5.0. Aliquot portions of this solution were heat-treated for 1 minute at 60°C, 70°C, 75°C and 80°C respectively. The results are shown in Table 2 and the results of the blank tests are also included. All figures are expressed as percentage as described in Example 1.

Example 3 and Comparative Example 3

A portion of microbial rennet was prepared by growing a culture of Mucor pusillus IAM F-27 in a sterilized liquid medium containing 10% wheat bran and 0.1% ammonium sulfate, under aerobic condition for 5 days at 30°C. The fermented broth was then filtered from the mycelium. One milliliter of this solution contained 0.4 CU of cellulase and 600 SU of milk-clotting enzyme.

This solution was heat-treated at 50°C for 5 minutes after the addition of 20% (weight/volume basis) sodium chloride and adjusting the pH to 5.0. About 60% of cellulase activity was lost by this treatment, while milk-clotting activity remained unchanged.

On the other hand, in a blank test without the addition of sodium chloride, both enzymes retained their full activities even after the treatment.

Example 4 and Comparative Example 4

A microbial rennet-containing liquid prepared as described in Example 1 was concentrated under reduced pressure to half of its volume. One milliliter of this concentrate contained 2.75 CU of cellulase and 52,000 SU of milk-clotting enzyme.

Sodium chloride was added to this solution in an amount of 10% and 20% respectively and each sample was heat-treated at 70°C for 1 minute after adjusting its pH to 5.0.

Cellulase and milk-clotting activities in the treated sample are shown in Table 3. The figures are expressed as percentage to the original activities. Comparative experiments were also carried out as described before, and the results are included in the same table.

Table 3

| | Comparative Example 4 | Example 4 Run 1 | Run 2 |
|---|---|---|---|
| NaCl (%) | 0 | 10 | 20 |
| Remaining cellulase activity | 50 | 16 | 3 |
| Remaining milk-clotting activity | 80 | 100 | 100 |

Table 2

| No. | NaCl (%) | Temperature | Run 1 60°C. | Run 2 70°C. | Run 3 75°C. | Run 4 80°C. |
|---|---|---|---|---|---|---|
| Comparative Example 2 | 0 | Remaining cellulase activity | 100 | 93 | 81 | 55 |
| | | Remaining milk-clotting activity | 100 | 98 | 70 | 8 |
| Example 2 | 20 | Remaining cellulase activity | 95 | 56 | 25 | 9 |
| | | Remaining milk-clotting activity | 100 | 100 | 96 | 90 |

Example 5 and Comparative Example 5

A microbial rennet-containing material was obtained by fractional precipitation with ethyl alcohol between 25 and 80% (volume/volume basis) of its concentration from the extracted enzyme liquid prepared as described in Example 1. To each aliquot of 10% (weight/volume basis) aqueous solution of dried powder of this material, sodium chloride was added to make 5, 10, 15 and 20% (weight/volume basis) respectively. Cellulase and milk-clotting activity were assayed and found to be 4.1 CU and 88,000 SU in 1 ml of this solution.

These samples were heat-treated at 65°C and 70°C for 5 minutes, after adjusting the pH to 5.0.

The results of this treatment are compared in Table 4 with those of the heat-treatment without sodium chloride.

All of these figures are expressed as percentage to the activities before the treatment.

Table 4

| Heating temperature | | Comparative Example 5 | Run 1 | Example 5 Run 2 | Run 3 |
|---|---|---|---|---|---|
| | NaCl | 0% | 10% | 15% | 20% |
| 65°C | Remaining cellulase activity | 27 | 5 | 2 | 1 |
| | Remaining milk-clotting activity | 42 | 97 | 100 | 100 |
| 70°C | Remaining cellulase activity | 10 | 4 | 2 | 1 |
| | Remaining milk-clotting activity | 1 | 75 | 89 | 92 |

Example 6 and Comparative Example 6

One gram of dried enzyme powder obtained in Example 5 contained 41 CU of cellulase and 880,000 SU of milk-clotting enzyme. To aliquots of 10 and 20% (weight/volume basis) aqueous solution of this powder was added sodium chloride to make 20% (weight/volume basis). After adjusting the pH to 5.0, the samples were heat-treated at 70°C for 1 minute, 3 minutes and 5 minutes respectively.

For comparison, samples of 10% and 20% enzyme solution were each heat-treated at 70°C for 3 minutes without the addition of sodium chloride.

All the results expressed as percentage to the original activities are shown in Table 5.

Table 5

| | Example 6 | | | | | | Comparative Example 6 | |
|---|---|---|---|---|---|---|---|---|
| Concentration of the microbial rennet | 10% | | | 20% | | | 10% | 20% |
| Heating time (minutes) | 1 | 3 | 5 | 1 | 3 | 5 | 3 | 3 |
| Remaining cellulase activity | 3 | 1 | trace | 1 | trace | trace | 35 | 25 |
| Remaining milk-clotting activity | 100 | 98 | 90 | 99 | 95 | 90 | 53 | 65 |

What we claim is:

1. A process for improving the quality of microbial rennet which can be used for making cheese from milk by inactivating cellulase impurities in microbial rennet which comprises heat-treating microbial rennet at a temperature of from about 45° to about 90°C. in an aqueous medium in the presence of at least 5% by weight of sodium chloride.

2. A process according to claim 1 wherein said heat-treatment is performed under thermostable pH conditions for the microbial rennet.

3. The process of claim 1 wherein the amount of sodium chloride is about 10 to 30 percent by weight.

4. The process of claim 1 wherein the heat treatment is performed at a temperature of from about 50° to about 80°C.

* * * * *